US012797064B2

(12) United States Patent
Azzara et al.

(10) Patent No.: US 12,797,064 B2
(45) **Date of Patent: *Nov. 17, 2026**

(54) SUTURING DEVICE

(71) Applicant: Durastat LLC, Austin, TX (US)

(72) Inventors: Adam Azzara, Austin, TX (US); Kevin T. Foley, Memphis, TN (US); Michael J. Milella, Jr., San Diego, CA (US)

(73) Assignee: Duastat LLC, Austin, TX (US)

( * ) Notice: Subject to any disclaimer, the term of this patent is extended or adjusted under 35 U.S.C. 154(b) by 147 days.

This patent is subject to a terminal disclaimer.

(21) Appl. No.: 18/904,414

(22) Filed: Oct. 2, 2024

(65) Prior Publication Data

US 2026/0090796 A1 Apr. 2, 2026

(51) Int. Cl.
*A61B 17/00* (2006.01)
*A61B 17/04* (2006.01)

(52) U.S. Cl.
CPC ...... *A61B 17/0469* (2013.01); *A61B 17/0487* (2013.01)

(58) Field of Classification Search
CPC . A61B 17/0491; A61B 17/04; A61B 17/0469; A61B 17/0483; A61B 17/0493; A61B 17/06066; A61B 2090/061; A61B 2017/047; A61B 2017/0496
USPC .......................................................... 606/144
See application file for complete search history.

(56) References Cited

U.S. PATENT DOCUMENTS

| | | | |
|---|---|---|---|
| 7,211,093 | B2 | 5/2007 | Sauer et al. |
| 8,398,657 | B2 | 3/2013 | Sauer |
| 8,864,777 | B2 | 10/2014 | Harrison et al. |
| 11,627,956 | B2 | 4/2023 | Nakadate et al. |
| 11,918,464 | B2 | 3/2024 | Sauer |
| 2006/0282098 | A1 | 12/2006 | Shelton, IV et al. |
| 2013/0146638 | A1 | 6/2013 | Mandakolathur Vasudevan et al. |
| 2015/0257753 | A1 | 9/2015 | Tang et al. |
| 2022/0338863 | A1 | 10/2022 | Harrison et al. |
| 2022/0354485 | A1 | 11/2022 | Rotem et al. |

OTHER PUBLICATIONS

International Search Report filed in PCT/US2025/047634 mailed Nov. 20, 2025.

*Primary Examiner* — Sana Sahand
(74) *Attorney, Agent, or Firm* — Rankin, Hill & Clark LLP

(57) ABSTRACT

A suturing device includes a first member, a suture connector holder, at least one carriage, and a receiver. The first member is elongate and includes a footplate extending from a distal end portion of the first member. The footplate includes a proximal face. The suture connector holder is formed with or connected to the footplate and is configured to retain a suture connector. The carriage includes a distal end face and is slidable with respect to the first member in a direction parallel to the first longitudinal axis. The proximal face and the distal end face define a tissue receiving gap in which tissue to be sutured is received between the proximal face and the distal end face. The receiver connects to the carriage and includes a suture connector capture configured to capture the suture connector. The thickness of the tissue being gripped by the suturing device can be measured.

17 Claims, 11 Drawing Sheets

SUTURING DEVICE

BACKGROUND

Suturing is a critical aspect of many surgical procedures, requiring precision and efficiency to minimize patient trauma and promote rapid healing. Traditional manual suturing can be time-consuming and may lead to inconsistent results, especially in minimally invasive procedures.

SUMMARY

In view of the foregoing, a suturing device includes a first member, a suture connector holder, a distal carriage connected with the first member, a proximal carriage connected with the first member, a receiver connectable to at least one of the distal carriage and the proximal carriage, and an elastic coupling that couples the distal carriage and the proximal carriage. The first member is elongate along a first longitudinal axis and includes a footplate extending from a distal end portion of the first member. The suture connector holder is formed with or connected to the footplate and is configured to retain a suture connector. The distal carriage is slidable with respect to the first member in a direction parallel to the first longitudinal axis. The proximal carriage is slidable with respect to the first member in a direction parallel to the first longitudinal axis. When the receiver is connected to at least one of the distal carriage and the proximal carriage, movement of the proximal carriage with respect to the first member results in movement of the receiver with respect to the first member. The receiver includes a suture connector capture configured to capture the suture connector. The elastic coupling is configured to compress when the distal carriage contacts an obstruction allowing the receiver to move with respect to the distal carriage and the first member.

According to another aspect, a suturing device can include a first member, a suture connector holder, at least one carriage, a receiver, and means for measuring a thickness of the tissue being gripped by the suturing device. The first member is elongate and includes a footplate extending from a distal end portion of the first member. The footplate includes a proximal face extending at an angle other than zero degrees to the first longitudinal axis. The suture connector holder is formed with or connected to the footplate and is configured to retain a suture connector. The carriage includes a distal end face and is connected with the first member and slidable with respect to the first member in a direction parallel to the first longitudinal axis. The proximal face and the distal end face define a tissue receiving gap in which tissue to be sutured is received between the proximal face and the distal end face. The receiver connects to the carriage and includes a distal edge configured to pierce the tissue and a suture connector capture configured to capture the suture connector. The means for measuring the thickness of the tissue being gripped by the suturing device can measure the distance between the proximal face of the footplate and the distal end face of the carriage.

DETAILED DESCRIPTION

Figure 1:
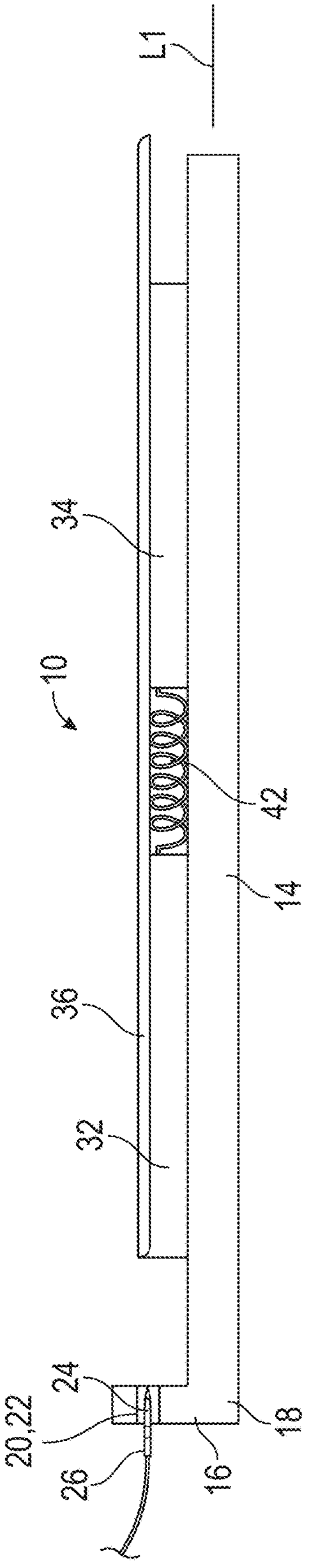
FIG. 1 is a schematic depiction of a suturing device.

Certain terminology is used in the following description for convenience only and is not limiting. The words "top", "bottom", "lower" and "upper" designate directions in the drawings to which reference is made. The words "distal" and "proximal" refer to directions away from and toward, respectively, an operator who is using the suturing devices described herein and related parts thereof. The terminology includes the above-listed words, derivatives thereof and words of similar import.

Figure 2:
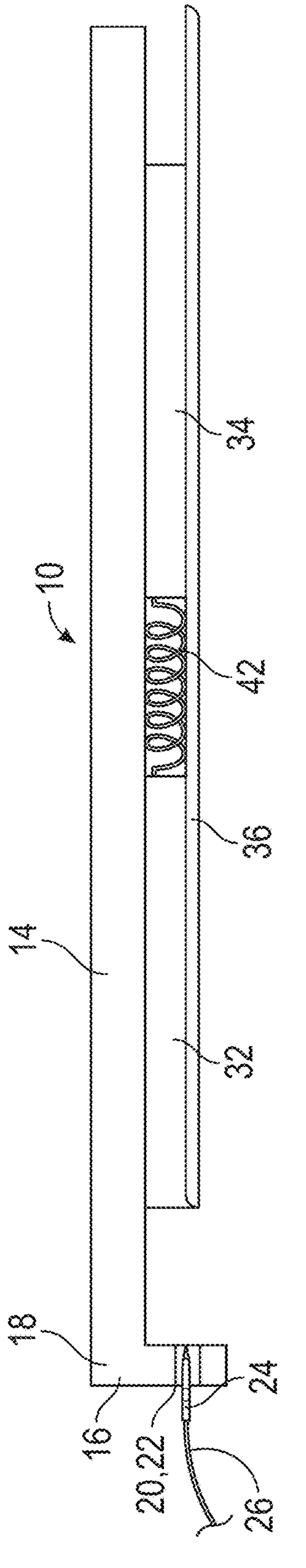
FIG. 2 is a schematic depiction of a similar suturing device as shown in FIG. 1.

FIGS. 1 and 2 depict a suturing device 10 including a first member 14 that is elongate along a first longitudinal axis L1. The first member 14 includes a footplate 16 extending transverse to the first longitudinal axis L1 from a distal end portion 18 of the first member 14. In FIG. 1, the footplate 16 extends upwardly from the distal end portion 18 of the first member 14, and in FIG. 2 the footplate 16 extends downwardly from the distal end portion 18 of the first member 14. In both instances the footplate 16 extends in a perpendicular direction from the first longitudinal axis L1, but it need not be exactly perpendicular to be transverse. The suturing device 10 also includes a suture connector holder 20 formed with or connected to the footplate 16. In the example shown in FIGS. 1 and 2, the footplate 16 includes a slot 22, which operates as the suture connector holder 20, configured to retain a suture connector 24 that is connected with a suture 26. The suture connector holder 20 could also be adhesive, a magnet, a clamp, a spring mechanism (e.g., a leaf spring) or combinations thereof located on the footplate 16 in a location similar to where the slot 22 is located in FIG. 1-3. The connector holder 20 could also be a blind hole extending through the footplate in the same direction as the slot 22 shown in FIG. 1-3.

A distal carriage 32 connects with the first member 14 and is slidable with respect to the first member 14 in a direction parallel to the first longitudinal axis L1. A proximal carriage 34 connects with the first member 14 and is slidable with respect to the first member 14 in a direction parallel to the first longitudinal axis L1. A receiver 36 is connectable to the distal carriage 32 and/or the proximal carriage 34. When connected, movement of the proximal carriage 34 with respect to the first member 14 results in movement of the receiver 36 with respect to the first member 14. The receiver

36 includes a suture connector capture 38 (see FIG. 3) configured to capture the suture connector 24.

Figure 3:
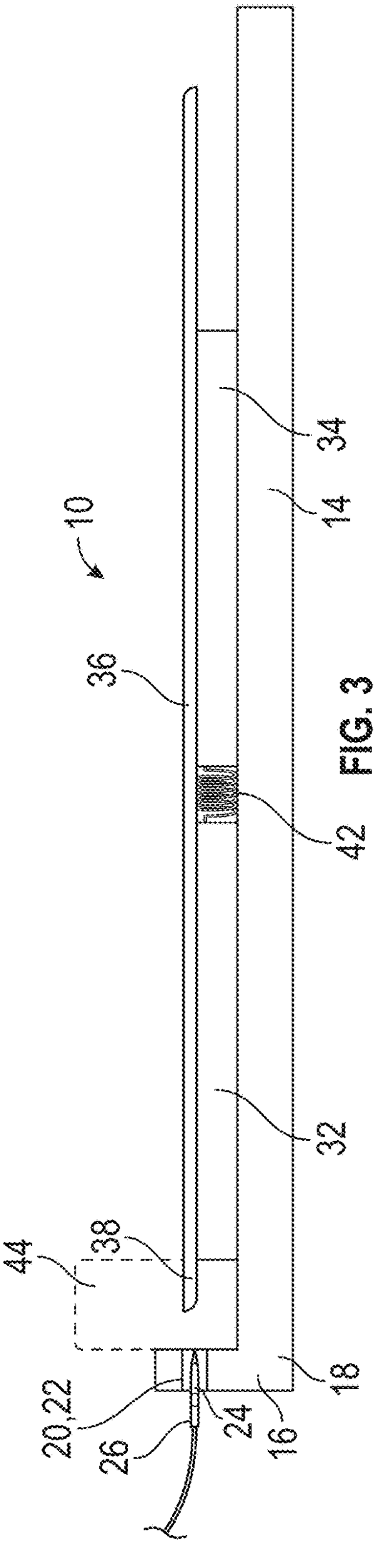
FIG. 3 is a schematic depiction of the suturing device in contact with an obstruction.

An elastic coupling 42 couples the distal carriage 32 and the proximal carriage 34. The receiver 36 in FIG. 1-3 is fixed to the proximal carriage 34 such that movement of the proximal carriage 34 results in movement of the receiver 36. The proximal carriage 34 can be moved with respect to the first member 14 in different manners, a more specific example of which being described below. As depicted in FIG. 3, the elastic coupling 42 is configured to compress when the distal carriage 32 contacts an obstruction 44 allowing the receiver 36 to move with respect to the distal carriage 32 and the first member 14 as the proximal carriage 34 continues to move with respect to the first member 14.

Figure 4:
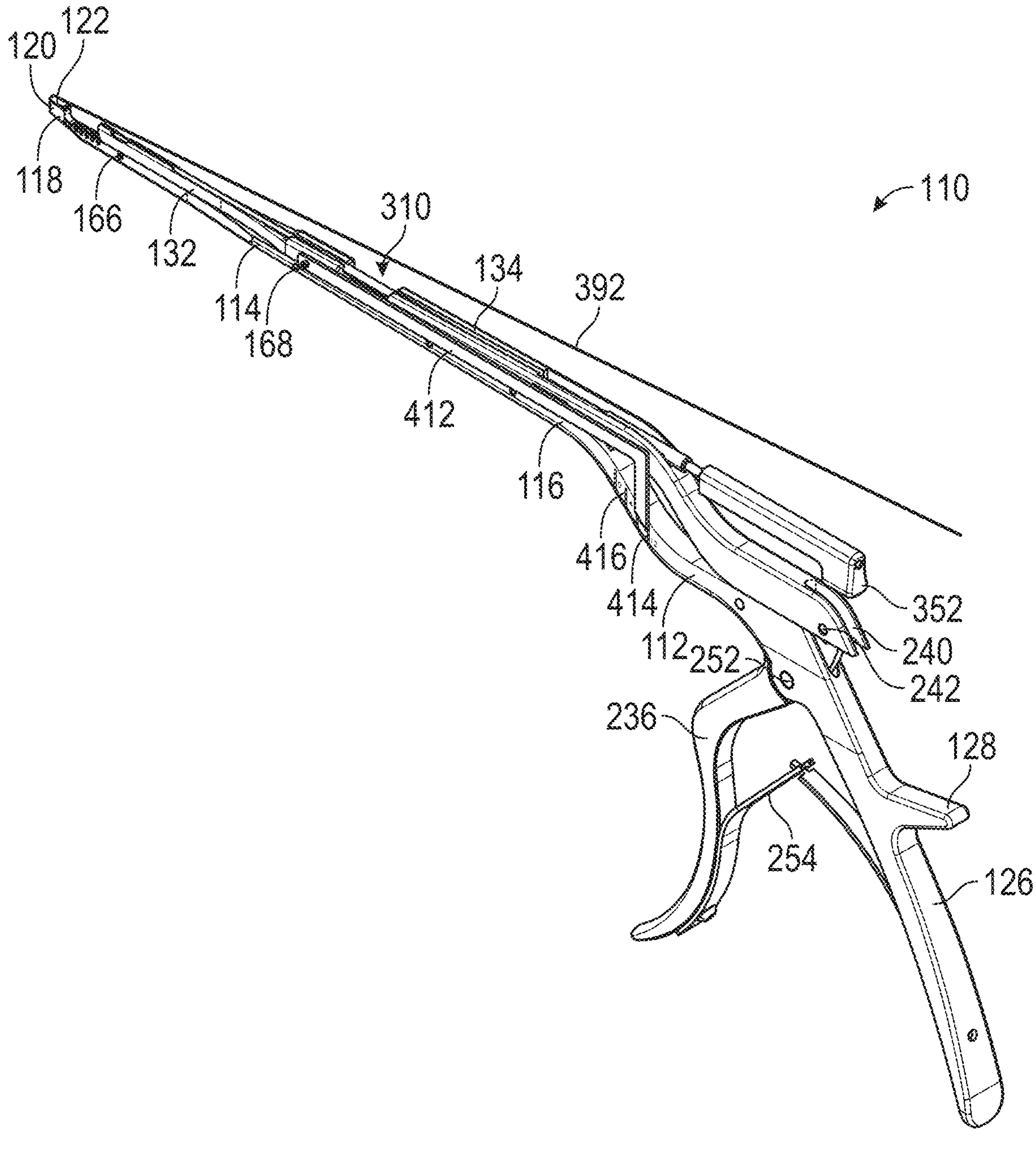
FIG. 4 is a perspective view of a more detailed example of a suturing device.
Figure 5:
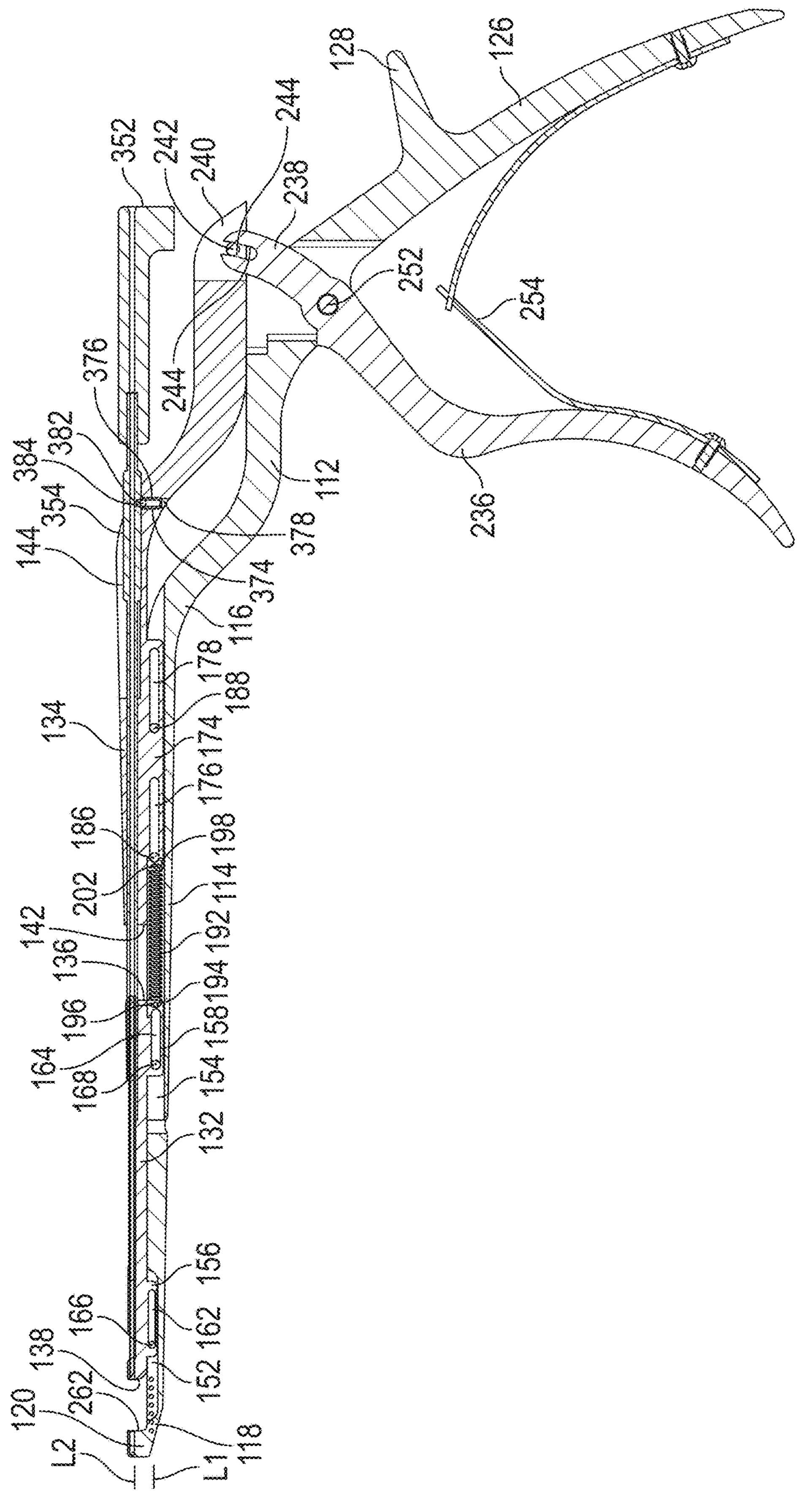
FIG. 5 is a cross-sectional view of the suturing device of FIG. 4.
Figure 6:
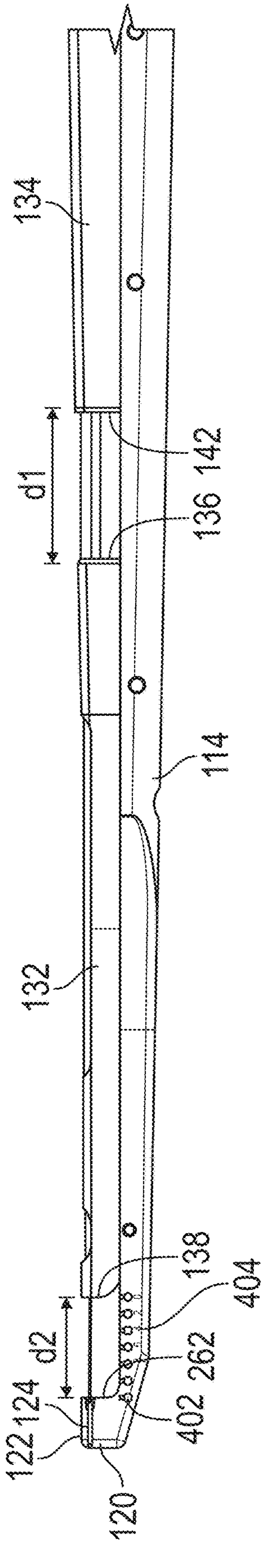
FIG. 6 is a side view of a distal portion of the suturing device of FIG. 4.
Figure 7:
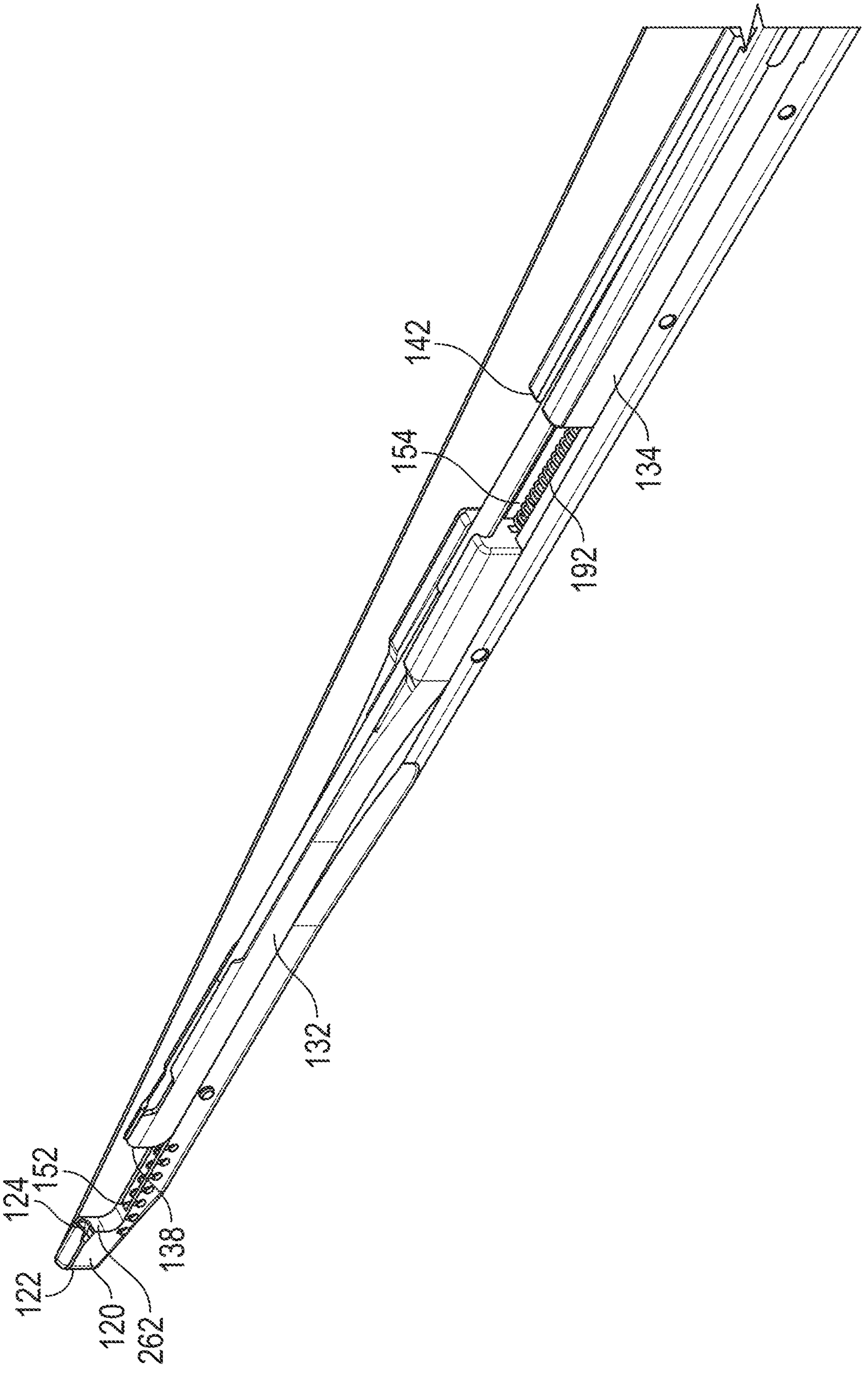
FIG. 7 is a perspective view of the distal portion of the suturing device of FIG. 4.

FIG. 4 depicts a more specific example of a suturing device 110 including a main body 112 having a first member 114 that is elongate along a first longitudinal axis L1 (FIG. 5) between a proximal portion 116 and a distal end portion 118. A footplate 120 is disposed at the distal end portion 18 of the first member 114. The footplate 120 extends upwardly from the distal end portion 118 and the first longitudinal axis L1 as illustrated in FIG. 5; however, the footplate 120 may extend downwardly similar to what is schematically depicted in FIG. 2. As illustrated in FIGS. 6 and 7, the footplate 120 includes a slot 122 configured to retain a suture connector 124. The slot 122 operates as a suture connector holder similar to the suture connector holder 20 described above with reference to FIGS. 1 and 2. In a similar fashion to the example shown in FIGS. 1 and 2, the suturing device 110 could include another type of suture connector holder formed with or connected to the footplate 120. The suture connector holder for the suturing device 110 could also be adhesive, a magnet, a clamp, a spring mechanism (e.g., a leaf spring) or combinations thereof located on the footplate 120 in a location similar to where the slot 122 is located in FIGS. 6 and 7. The connector holder could also be a blind hole extending through the footplate in the same direction as the slot 122 shown in FIG. 6.

With reference back to FIGS. 4 and 5, the main body 112 includes a handle 126 that extends downwardly includes a proximal extension 128. The handle 126 is shown integral with main body 112, but could be a separate part connected with the main body 112. The main body 112 is also shown as having a bayonet configuration, but could be straight similar in configuration to a typical Kerrison Rongeur.

With reference back to FIG. 4, the suturing device 110 also includes a distal carriage 132 and a proximal carriage 134. With reference to FIG. 5, the distal carriage 132 is elongate along a second longitudinal axis L2 between a proximal end face 136 and a distal end face 138. The proximal carriage 134 is elongate along the second longitudinal axis L2 between a distal end surface 142 and a proximal section 144 prior to bending toward the bayonet configuration. The second longitudinal axis L2 is substantially parallel to the first longitudinal axis L1 so that both the distal carriage 132 and the proximal carriage 134 are connected with the main body 112 and slidable with respect to the first member 114 in a direction parallel to the first longitudinal axis L1.

With reference to FIGS. 5 and 7, the first member 114 includes a distal channel 152 and a proximal channel 154 that are both elongated along the first longitudinal axis L1. With reference to FIG. 5, the distal carriage 132 includes a downwardly depending distal lobe 156 that extends into the distal channel 152 and a downwardly depending proximal lobe 158 that extends into the proximal channel 154. A first elongate opening 162 is provided in the downwardly depending distal lobe 156 and a second elongate opening 164 is provided in the downwardly depending proximal lobe 158. A first pin 166 extends through the first member 114 (see FIG. 4) and the first elongate opening 162 and a second pin 168 extends through the first member 114 and the second elongate opening 164 to connect the distal carriage 132 to the first member 114. The cross section of the first pin 166 and the second pin 168, the length of the downwardly depending distal lobe 156 and the downwardly depending proximal lobe 158, the length of each of the first elongate opening 162 and the second elongate opening 164 and the length of the distal channel 152 and the proximal channel 154 allow for the distal carriage 132 to travel with respect to the first member 114 such that the distal end face 138 can contact the footplate 120. The movement of the distal carriage 132 with respect to the first member 114 will be described in more detail below.

The proximal carriage 134 includes a downwardly depending lobe 174 that extends into the proximal channel 154. A first elongate hole 176 and a second elongate hole 178 are provided in the downwardly depending lobe 174. A third pin 186 extends through the first member 114 (see FIG. 4) and the first elongate hole 176 and a fourth pin 188 extends through the first member 114 and the second elongate hole 178 to connect the proximal carriage 134 to the first member 114. The cross section of the third pin 186 and the fourth pin 188, the length of the downwardly depending lobe 174, the length of each of the first elongate hole 176 and the second elongate hole 178, and the length of the proximal channel 154 are designed to allow for the proximal carriage 134 to travel along the first member 114.

With reference to FIGS. 5 and 7, an elastic coupling 192 couples the distal carriage 132 and the proximal carriage 134. In the illustrated embodiment, the elastic coupling 192 is a metal coil compression spring; however, another elastic device capable of performing the functions described herein could also be used. With reference to the embodiment illustrated in FIG. 5, a distal spring fastener 194, which can be a pin, connects a distal end 196 of the elastic coupling 192 to the distal carriage 132 at the downwardly depending proximal lobe 158 and a proximal spring fastener 198, which can also be a pin, connects a proximal end 202 of the elastic coupling 192 to the proximal carriage 134 at the downwardly depending lobe 174.

With reference to FIGS. 4 and 5, a lever 236 is operatively connected with the proximal carriage 134 and the main body 112. Movement of the lever 236 with respect to the main body 112 results in movement of the proximal carriage 134 with respect to the first member 114. An upper end portion 238 of the lever 236 is received in a cut out 240 provided in the proximal carriage 134. A connecting pin 242, which is fixed to the proximal carriage 134 within the cut out 240, is received in a notch 244 provided in the upper end portion 238 of the lever 236 to connect the lever 236 with the proximal carriage 134. A pivot pin 252 attaches the lever 236 to the main body 112 and/or the handle 126. A damper 254, such as a leaf spring, is disposed between the handle 126 and the lever 236. In use, the lever 236 is actuated (squeezed) to move the proximal carriage 134 with respect to the main body 112. As the lever 236 pivots toward handle 126, the proximal carriage 134 slides along the second longitudinal axis L2 towards the footplate 120.

The elastic coupling 192 is configured to allow the distal carriage 132 and the proximal carriage 134 to move together with respect to the first member 114. More specifically, the elastic coupling 192 is configured to maintain a predetermined distance between the distal carriage 132 and the proximal carriage 134 as the lever 236 is being moved with respect to the main body 112 until the distal carriage 132 becomes obstructed. With reference to FIGS. 5, 6 and 7, the footplate 120 includes a proximal face 262. The proximal face 262 extends at an angle other than zero degrees to the first longitudinal axis L1. In FIG. 5, the proximal face 262 is shown as being disposed perpendicular to the first longitudinal axis L1, but it could be disposed at an acute or obtuse angle with respect to the first longitudinal axis L1. Prior to movement of the lever 236, the distal end surface 142 of the proximal carriage 134 is spaced a first distance d1 (FIG. 6) from the proximal end face 136 of the distal carriage 132 and the proximal face 262 of the footplate 120 is spaced a second distance d2 from the distal end face 138 of the distal carriage 132. The second distance d2 is less than the first distance d1. The second distance d2 also defines a tissue receiving gap in which tissue to be sutured is received between the proximal face 262 and the distal end face 138.

With reference back to FIG. 4, a receiver 310 is connectable to at least one of the distal carriage 132 and the proximal carriage 134 such that when connected movement of the proximal carriage 134 with respect to the first member 114 results in movement of the receiver 310 with respect to the first member 114. With reference to FIGS. 8 and 9A-9E, the receiver 310 includes a distal edge 312 configured to pierce tissue, which is depicted in phantom in FIG. 9A-9E, and a suture connector capture 314 configured to capture the suture connector 124.

Figure 8:
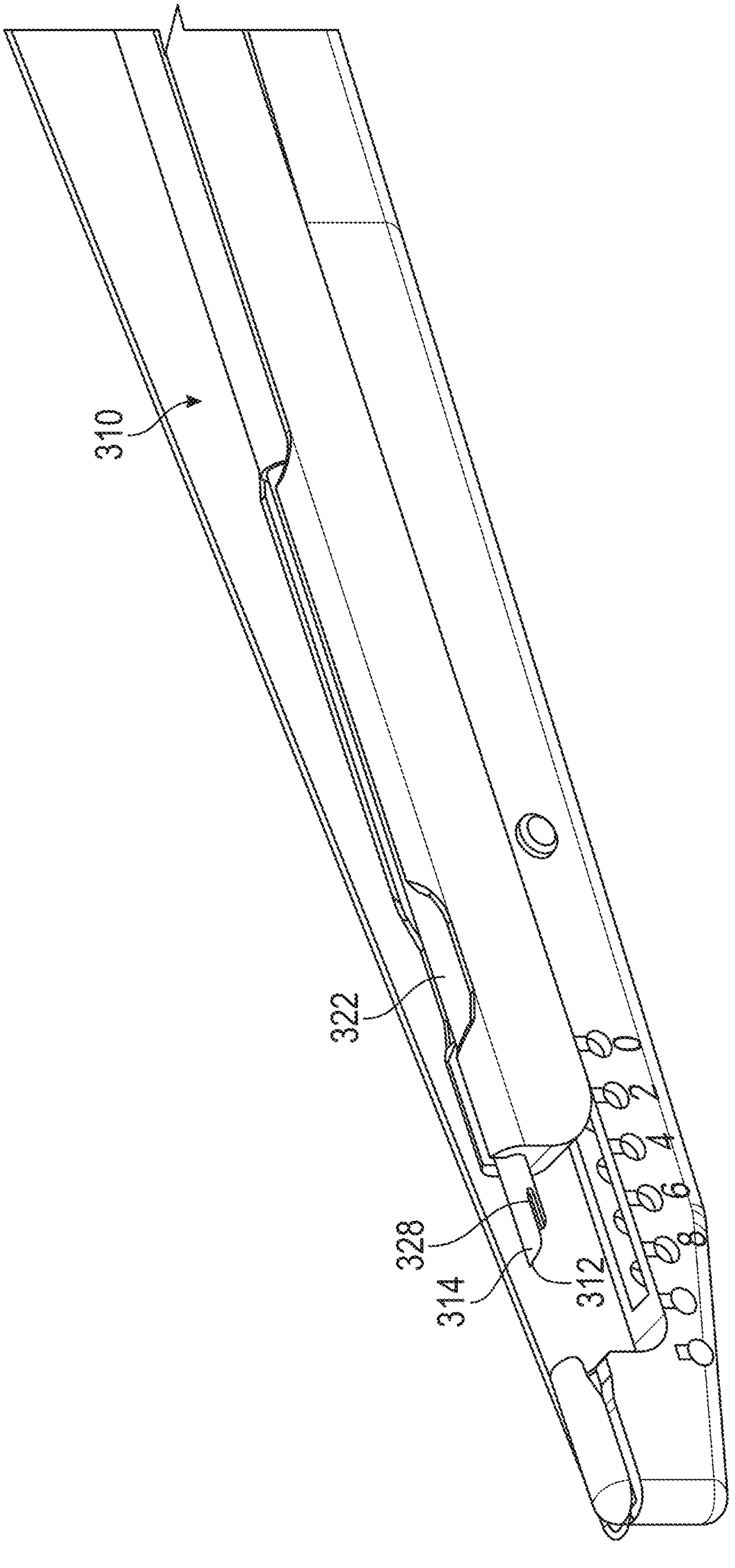
FIG. 8 is another perspective view of the distal portion of the suturing device of FIG. 4.
Figure 10:
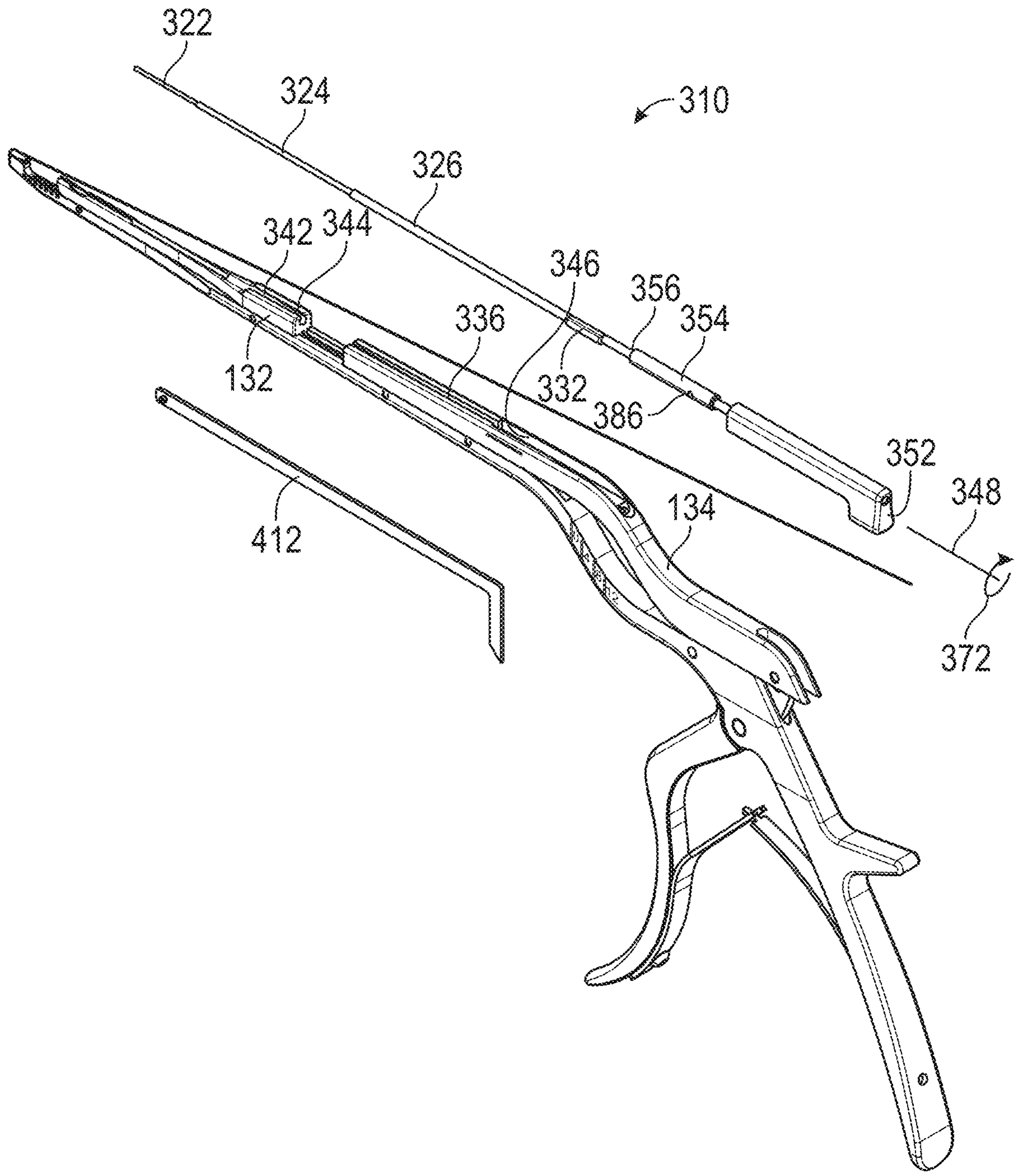
FIG. 10 is a perspective view of the suturing device of FIG. 4 with a caliper jaw and a receiver having been removed.

With reference to FIG. 10, the receiver 310 includes a shaft, which in the illustrated embodiment is made up of a shaft assembly including a hypotube 322, a central shaft 324 and a proximal shaft 326, elongate parallel to the first longitudinal axis L1 along the second longitudinal axis L2. The hypotube 322 is distal most and includes the distal edge 312 and the suture connector capture 314. With reference to FIG. 8, the hypotube 322 can include a distal notch 328, which allows the hypotube 322 to deform outwardly when receiving the suture connector 124 so as to capture the suture connector 124. The central shaft 324 connects the proximal shaft 326 to the hypotube 322.

Figure 11:
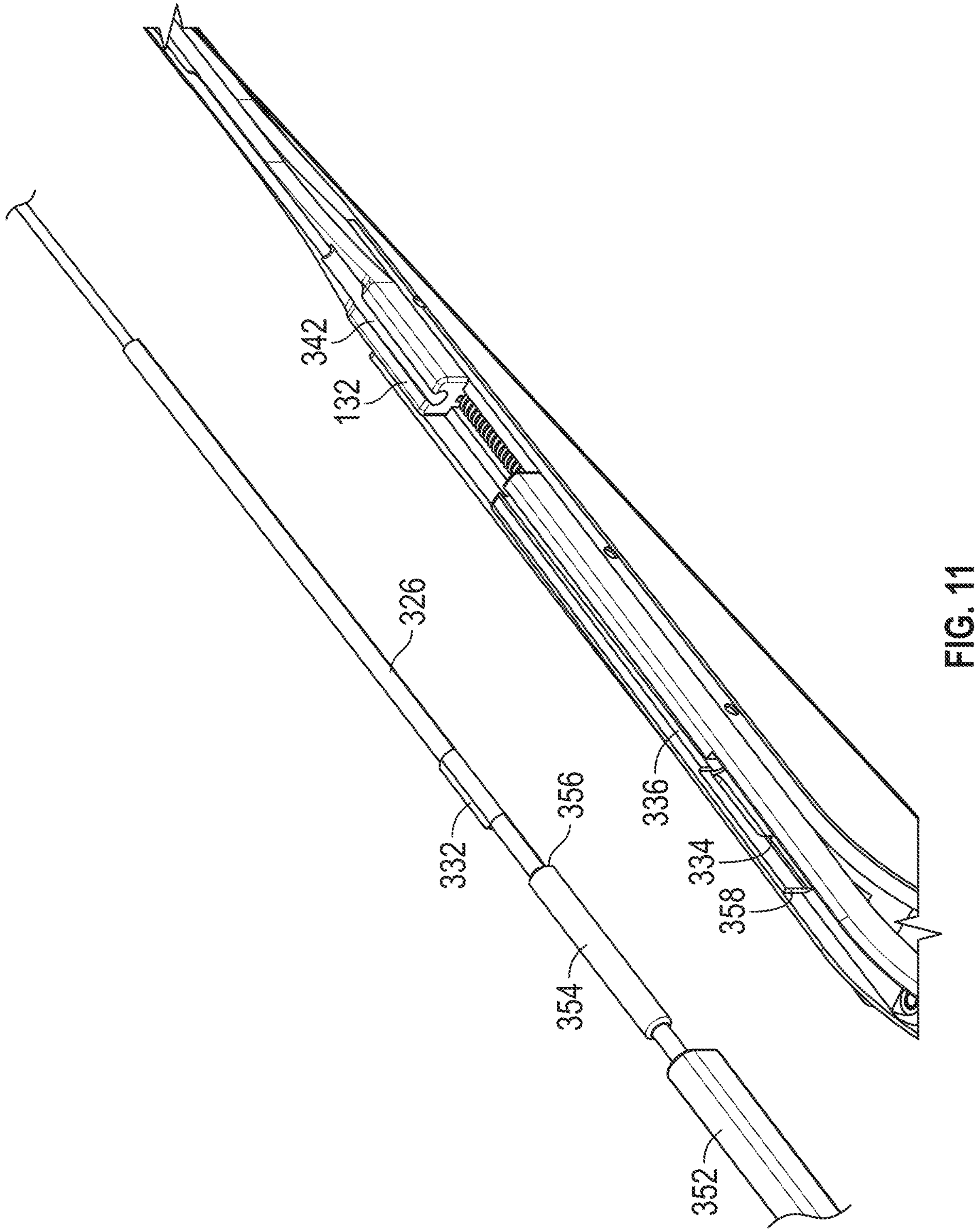
FIG. 11 a perspective view of a distal portion of the suturing device of FIG. 4 with the receiver having been removed.

With continued reference to FIG. 10, the receiver 310 and the proximal carriage 134 include locking features that inhibit translation of the receiver 310 with respect to the proximal carriage 134 in any one of three orthogonal planes when the receiver 310 is connected with the proximal carriage 134. With reference to FIGS. 10 and 11, the locking features include a radial protrusion 332 extending from the shaft, and more particularly the proximal shaft 326, and locking channel 334 provided in the proximal carriage 134 that receives the radial protrusion 332 when the receiver 310 is connected with the proximal carriage 134. With reference to FIG. 11, the proximal carriage 134 includes a proximal carriage channel 336 configured to receive the receiver 310. The locking channel 334 is positioned within the proximal carriage channel 336. The distal carriage 132 includes a distal carriage channel 342 configured to receive the receiver 310.

With reference to FIG. 10, the distal carriage channel 342 includes an open top 344. The proximal carriage channel 336 includes an upper opening 346. The receiver 310 is disconnectable from the distal carriage channel 342 through the open top 344 and is disconnectable from the proximal carriage channel 336 through the upper opening 346. The receiver 310 is rotatable with respect to the proximal carriage 134 and the distal carriage 132 about a rotational axis 348 parallel to the first longitudinal axis L1. The receiver 310 includes a knob 352 connected with the proximal shaft 326 to facilitate rotation. The receiver 310 is rotated with respect to the proximal carriage 134 and the distal carriage 132 about the rotational axis 348 prior to disconnecting the receiver 310 from the proximal carriage 134 and the distal carriage 132.

With continued reference to FIG. 10, the receiver 310 also includes a protruding cylindrical section 354 on the proximal shaft 326. With reference to FIG. 11, a distal shoulder 356 where the protruding cylindrical section 354 transitions to the smaller diameter portion of the proximal shaft 326 contacts a shoulder 358 within the proximal carriage channel 336 to inhibit movement of the receiver 310 with respect to the proximal carriage 134 along the second longitudinal axis L2 when the receiver 310 is connected to the proximal carriage 134. With reference to FIGS. 5 and 10, the proximal carriage 134 and the receiver 310 include a detent mechanism to provide an indication to the operator that the receiver 310 is in each of a use position, which is shown in FIG. 1, and a position in which the receiver 310 is disconnectable from the proximal carriage 134, which is when the knob 352 has been rotated 270 degrees from the location shown in FIG. 10 in the direction of arrow 372. With reference to FIG. 5, a spring 374 provided within a housing 376 is inserted (threaded) into a hole 378 provided in the proximal carriage 134. The spring 374 biases a ball 382 toward the protruding cylindrical section 354 on the proximal shaft 326. The ball 382 is selectively receivable in a first depression 384 (FIG. 5) formed in the protruding cylindrical section 354 when the receiver 310 is in the use position and a second depression 386 (FIG. 10) formed in the protruding cylindrical section 354 when the receiver 310 is in the position in which it can be removed from the proximal carriage 134 and the distal carriage 132.

Figure 9A:
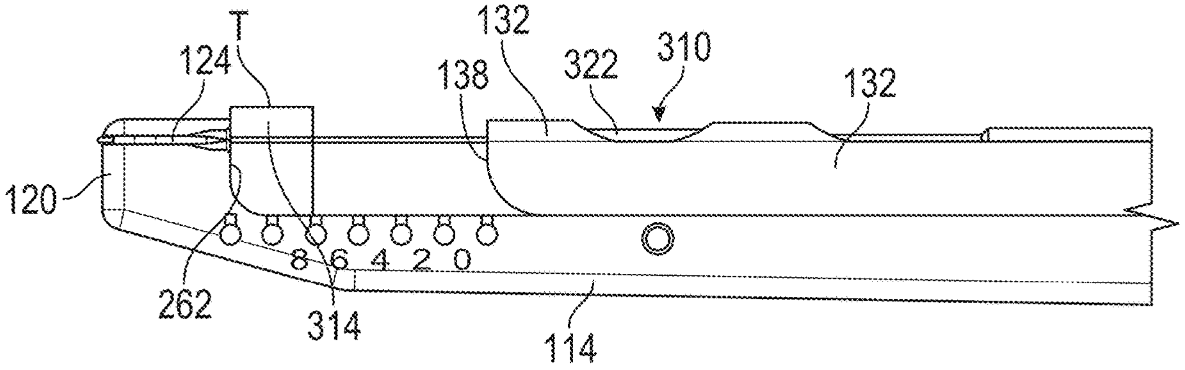
FIG. 9A-9E are side views of the distal portion of the suturing device of FIG. 4 showing different stages of a suturing process.
Figure 9B:
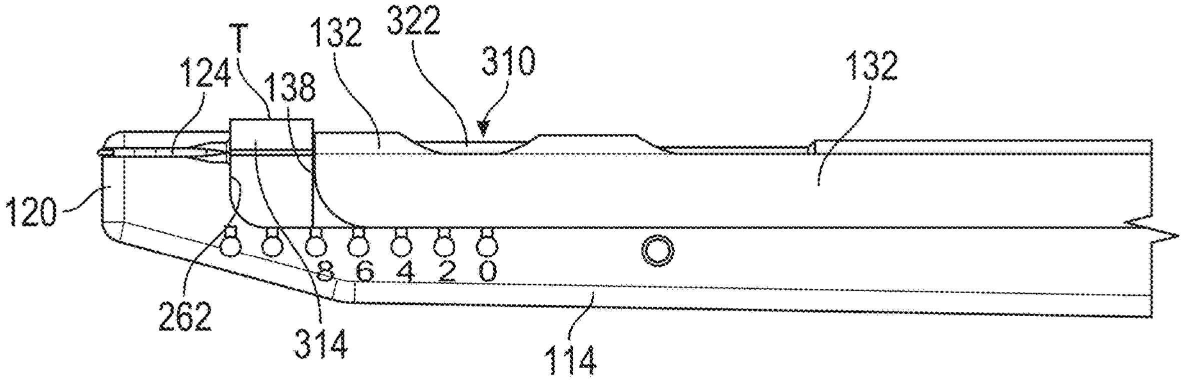
Figure 9C:
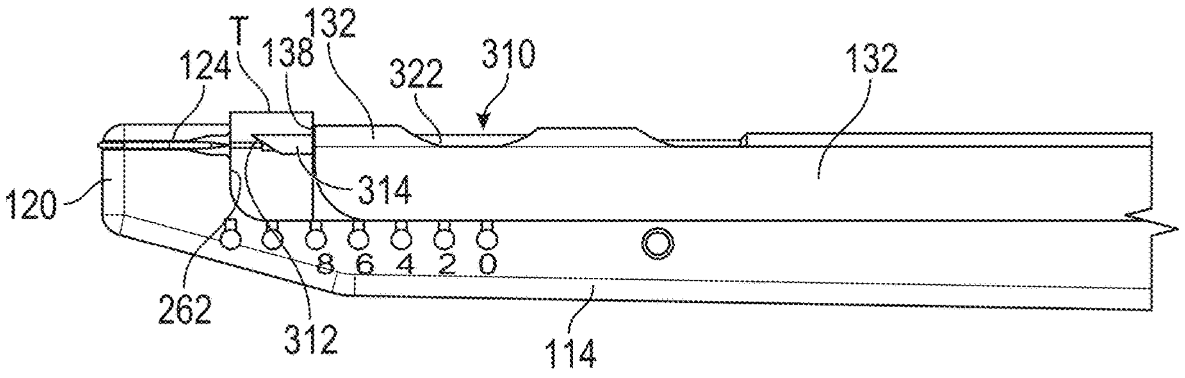
Figure 9D:
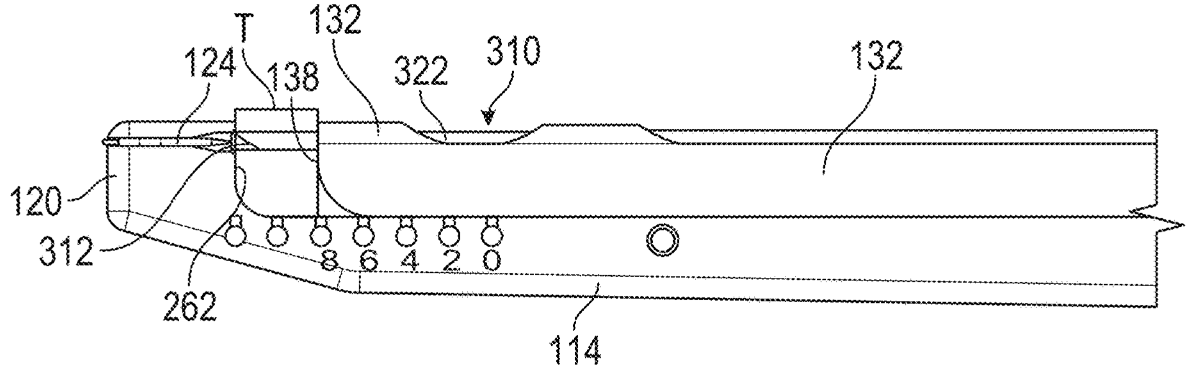
Figure 9E:
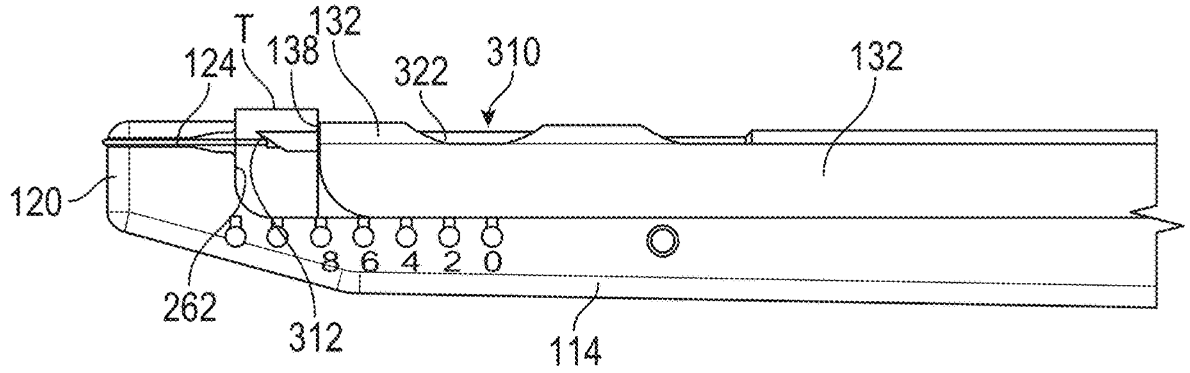

Operation of the suturing device 110 will be described with reference to FIG. 9A-9E. The suturing device 110 is shown in the open position in FIG. 9A with the receiver 310 appropriately connected with the distal carriage 132 and the proximal carriage 134 and the knob 352 in the position shown in FIG. 1. Tissue T to be sutured is brought in contact with the proximal face 262 of the footplate 120. When in the open position, the distal edge 312 of the receiver 310 can be offset in a proximal direction from the distal end face 138 prior to the distal carriage 132 contacting the tissue T. The lever 236 (FIG. 1) is then squeezed resulting in the distal carriage 132, the proximal carriage 134 and the receiver 310 moving with respect to the first member 114 until the distal end face 138 of the distal carriage 132 contacts the tissue T, which is about to happen in FIG. 9B. As mentioned above, the elastic coupling 192 maintains a predetermined distance between the distal carriage 132 and the proximal carriage 134 as the lever 236 is being squeezed until the distal carriage 132 becomes obstructed. The tissue T acts as an obstruction to obstruct the distal carriage 132. The elastic coupling 192 then compresses when the distal end face 138 of the distal carriage 132 contacts the tissue T allowing the distal edge 312 of the receiver 310 to extend beyond the distal end face 138 to pierce the tissue T, which is shown in FIG. 9C. The receiver 310 continues to drive forward toward the footplate 120 piercing the tissue T and is received in the slot 122, which is shown in FIG. 9D. When the distal carriage 132 compresses the tissue T to the point where the proximal carriage 134 starts moving forward, as the lever 236 is continued to be squeezed, the elastic coupling 192 will eventually reach its minimum length, or "bottom out", at which time the full force applied by the lever 236 along the second longitudinal axis L2 is being applied to the distal carriage 132. The suture connector 124 is then received in the hypotube 322 and engages the suture connector capture 314. The lever 236 is then released and biased toward the position shown in FIG. 4 by the damper 254, which pulls the suture connector 124 and a suture 392 attached to the suture connector 124 through the tissue T. The suture connector 124 is provided to facilitate coupling the suture 392 to the receiver 310 and is depicted as a surgical needle in FIG. 9A-9E; however, the suture connector 124 can be in the form of other items that can connect with a surgical suture including a plug, a ferrule, a shaft, a ball, a cylindrical member and the like. Providing the suture connector 124 as a surgical needle, however, provides a tapered surface to facilitate insertion into the hypotube 322. If desired, however, the hypotube 322 of receiver 310 could be in the form of a needle or similar tapered shaft and the suture connector 124 could be in the form of a female receptacle that receives the tapered shaft so as to couple the suture 392 to the receiver 310.

The suturing device 110 can also include means for measuring a thickness of the tissue being gripped by the suturing device 110. This can be useful to allow an operator of the suturing device 110 to measure the thickness of the tissue through which the suture 392 is to be passed prior to passing the suture 392 through the tissue. An operator of the suturing device 110 can first compress the tissue between the between the proximal face 262 of the footplate 120 and the distal end face 138 of the distal carriage 132 to measure the thickness of the tissue, and then pass the suture 392 through the tissue.

With reference to FIGS. 6 and 7, indicia can be provided on the suturing device to indicate the thickness of tissue T being gripped between the proximal face 262 of the footplate 120 and the distal end face 138 of the distal carriage 132. For example, the main body 112, or more particularly the first member 114, includes a plurality of measurement openings 402 positioned between the proximal face 262 and the distal end face 138 prior to movement of the lever 236, or prior to movement of the distal carriage 132 with respect to the first member 114. The measurement openings 402, which are radiolucent, can be particularly useful when used during a fluoroscopy procedure because the measurement openings 402 will be visible as compared to the solid portion of the main body 112, which can be made from stainless steel, in which the measurement openings 402 are provided. Graduation markings 404 can be provided on the main body 112, or more particularly the first member 114, and be associated with respective measurement openings 402. The graduation markings 404 can be in the form of numbers or tick marks. The graduation markings 404 could also be provided on the main body 112, or more particularly the first member 114, without the measurement openings 402. For example, if the main body 112 were made from a radiolucent material, e.g. plastic, the graduation markings 404 could be made from a radiopaque material, e.g., tantalum.

With reference to FIG. 4, a caliper jaw 412 can be connected with the distal carriage 132 and movable with respect to the main body 112 and the first member 114 along with the distal carriage 132. The caliper jaw 412 includes a measurement surface 414, which can be a point or a vertical line similar to that shown in FIG. 1. Graduation indicia 416 are provided on the main body 112. Due to the connection between the distal carriage 132 and the caliper jaw 412, the measurement surface 414 aligns with a respective graduation indicia 416 to indicate a distance between the proximal face 262 and the distal end face 138, which can also provide an indication of the thickness of tissue T being gripped between the proximal face 262 of the footplate 120 and the distal end face 138 of the distal carriage 132.

When both of the aforementioned means for measuring the thickness of the tissue being gripped by the suturing device 110 are provided, there is a redundancy in the measurement, which may be a useful check. In some instances, however, only one of the aforementioned means for measuring the thickness of the tissue being gripped by the suturing device 110 may be provided.

Figure 12:
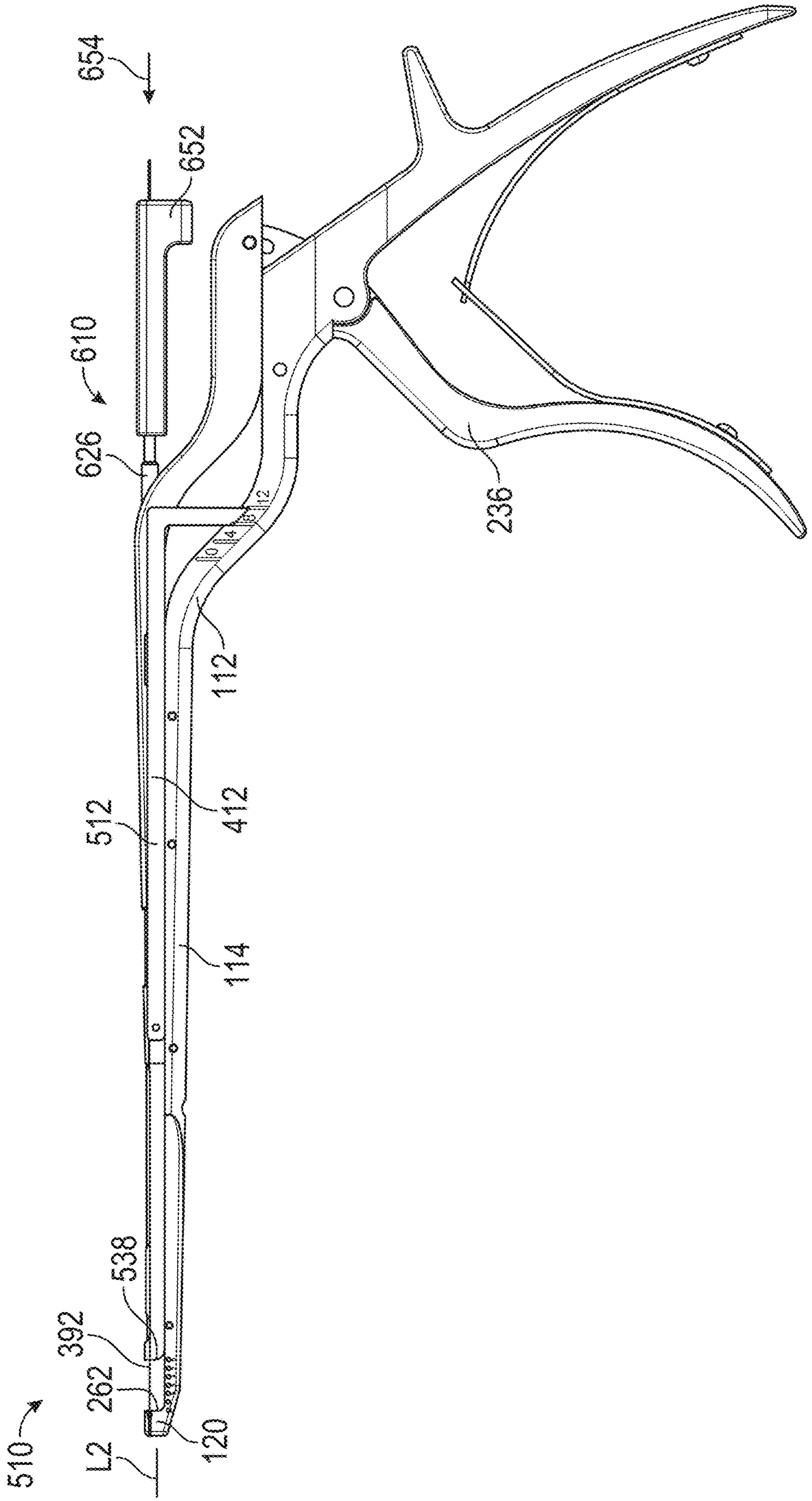
FIG. 12 is a side view of another example of a suturing device.

FIG. 12 depicts an alternative suturing device 510 that operates slightly differently than the suturing device 110 while still being able to measure the thickness of the tissue being gripped by the alternative suturing device 510 before passing the suture 392 through the tissue. The alternative suturing device 510 includes the same or very similar main body 112 as the suturing device 110 described above; therefore further explanation thereof will be omitted. The alternative suturing device 510 also includes the same or very similar lever 236 as the suturing device 110 described above; therefore further explanation thereof will be omitted.

The alternative suturing device 510 differs from the suturing device 110 described above in that the elastic coupling 192 coupling the distal carriage 132 to the proximal carriage 134 is omitted in the alternative suturing device 510. The alternative suturing device 510 includes a carriage 512 that is about as long as the entire length (measured along the second longitudinal axis L2) as the distal carriage 132, the elastic coupling 192 and the proximal carriage 134 in the suturing device 110 described above. The carriage 512 includes a distal end face 538 similar to the distal end face 138 of the distal carriage 132 described above. The carriage 512 also connects with the lever 236 in a similar manner that the proximal carriage 134 is connected with the lever 236 (see FIG. 5).

The alternative suturing device 510 also differs from the suturing device 110 described above in that it includes an alternative receiver 610 that is connectable to the carriage 512. When the alternative receiver 610 is connected to the carriage 512, however, movement of the carriage 512 with respect to the first member 114 does not result in movement of the alternative receiver 610 with respect to the first member 114. The alternative receiver 610 can be similar to the receiver 310 described above in that it can include a shaft assembly including a hypotube (not visible but similar to the hypotube 322), a central shaft (not visible but similar to the central shaft 324) and a proximal shaft 626 (similar to the proximal shaft 326). The alternative receiver 610 is elongate along the second longitudinal axis L2 where the hypotube is distal most and includes the distal edge and the suture connector capture similar to the hypotube 322 described above. The alternative receiver 610 can also include a knob 652 similar to the knob 352 described above.

The alternative receiver 610 and the carriage 512 can include locking features that inhibit translation of the alternative receiver 610 with respect to the carriage 512 in two orthogonal planes that are each perpendicular to the second longitudinal axis L2 when the alternative receiver 610 is connected with the carriage 512. But, the carriage 512 can move with respect to the alternative receiver 610 and the first member 114 along the second longitudinal axis L2 when the lever 236 is squeezed. Accordingly, tissue can be gripped between the proximal face 262 and the distal end face 538 similar to the suturing device 110 without the alternative receiver 610 moving with respect to the first member 114.

To pass the suture 392, however, the alternative receiver 610 is moved along the second longitudinal axis L2 relative to the carriage 512, for example by the operator pressing on the knob 652 in the direction of arrow 654. The alternative receiver 610 can be moved along the second longitudinal axis L2 relative to the carriage 512 in other manners, e.g., another lever or trigger similar to the lever 236 could connect with the alternative receiver 610 and be squeezed to move the alternative receiver 610. The alternative receiver 610 is removable from the carriage 512 in a similar manner that the receiver 310 is removable from the proximal carriage 134.

The alternative suturing device 510 can also include similar means for measuring the thickness of the tissue being gripped by the alternative suturing device 510. In the alternative suturing device 510, however, the caliper jaw 412 is connected to carriage 512 for movement with the carriage 512.

It will be appreciated that various of the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A suturing device comprising:

a first member elongate along a first longitudinal axis including a footplate extending from a distal end portion of the first member, the footplate including a proximal face extending at an angle other than zero degrees to the first longitudinal axis;

a suture connector holder formed with or connected to the footplate and being configured to retain a suture connector;

at least one carriage including a distal end face and being connected with the first member and slidable with respect to the first member in a direction parallel to the first longitudinal axis, wherein the proximal face and the distal end face define a tissue receiving gap in which tissue to be sutured is received between the proximal face and the distal end face;

a receiver connectable to the at least one carriage, wherein the receiver includes a suture connector capture configured to capture the suture connector; and means for measuring a thickness of the tissue being gripped between the proximal face of the footplate and the distal end face of the at least one carriage.

2. The suturing device of claim 1, wherein the means for measuring the thickness of the tissue being gripped between the proximal face of the footplate and the distal end face of the at least one carriage includes a plurality of measurement openings provided on the first member.

3. The suturing device of claim 2, further comprising:

a main body including the first member; and a lever operatively connected with the at least one carriage and the main body, movement of the lever with respect to the main body results in movement of the at least one carriage with respect to the first member;

wherein the plurality of measurement openings are positioned between the proximal face and the distal end face prior to movement of the lever.

4. The suturing device of claim 2, wherein the means for measuring the thickness of the tissue being gripped between the proximal face of the footplate and the distal end face of the at least one carriage further includes at least one graduation marking provided on the first member and associated with at least one measurement opening of the plurality of measurement openings.

5. The suturing device of claim 1, wherein the means for measuring the thickness of the tissue being gripped between the proximal face of the footplate includes graduation markings provided on the first member.

6. The suturing device of claim 5, wherein the graduation markings are radiolucent and the first member is radiopaque.

7. The suturing device of claim 5, wherein the graduation markings are radiopaque and the first member is radiolucent.

8. The suturing device of claim 1, wherein the means for measuring the thickness of the tissue being gripped between the proximal face of the footplate and the distal end face of the at least one carriage further includes a caliper jaw connected with the at least one carriage and movable along with the at least one carriage and with respect to the first member.

9. The suturing device of claim 8, further comprising:

a main body including the first member; and wherein the caliper jaw includes a measurement surface and the means for measuring the thickness of the tissue being gripped between the proximal face of the footplate and the distal end face of the at least one carriage further includes graduation indicia provided on the main body, wherein the measurement surface aligns with a respective graduation indicia to indicate a distance between the proximal face and the distal end face.

10. The suturing device of claim 9, wherein the at least one carriage includes distal carriage having the distal end face and a proximal carriage connected with the first member and slidable with respect to the first member in the direction parallel to the first longitudinal axis, the suturing device further comprising an elastic coupling that couples the distal carriage and the proximal carriage, wherein the caliper jaw is connected with the distal carriage and movable along with the distal carriage and with respect to the first member.

11. The suturing device of claim 1, wherein the at least one carriage includes distal carriage having the distal end face and a proximal carriage connected with the first member and slidable with respect to the first member in the direction parallel to the first longitudinal axis, the suturing device further comprising an elastic coupling that couples the distal carriage and the proximal carriage, wherein the elastic coupling is configured to allow the distal carriage and the proximal carriage to move together with respect to the first member.

12. The suturing device of claim 11, further comprising:

a main body including the first member; and a lever operatively connected with the at least one carriage and the main body, movement of the lever with respect to the main body results in movement of the at least one carriage with respect to the first member, wherein the elastic coupling is configured to maintain a predetermined distance between the distal carriage and the proximal carriage as the lever is being moved with respect to the main body until the distal carriage becomes obstructed.

13. The suturing device of claim 12, wherein the elastic coupling is configured to compress when a distal end face of the distal carriage contacts the tissue allowing a distal edge of the receiver to extend beyond the distal end face to pierce the tissue.

14. The suturing device of claim 1, wherein the receiver and the at least one carriage include locking features that inhibit translation of the receiver with respect to the at least one carriage in two orthogonal planes that are each perpendicular the first longitudinal axis.

15. The suturing device of claim 1, wherein the suture connector holder is a slot formed in the footplate.

16. The suturing device of claim 1, wherein the suture connector holder is adhesive, a magnet, a clamp, a spring mechanism or combinations thereof located on the footplate.

17. The suturing device of claim 1, wherein the suture connector holder is a blind hole formed in the footplate.

* * * * *